(12) United States Patent
Thakur et al.

(10) Patent No.: US 9,545,402 B2
(45) Date of Patent: Jan. 17, 2017

(54) PHARMACEUTICAL COMPOSITIONS COMPRISING 4-AMINO-5-FLUORO-3-[6-(4-METHYLPIPERAZIN-1-Y1)-1H-BENZIMIDAZOL-2-Y1]-1H-QUINOLIN-2-ONE LACTATE MONOHYDRATE

(75) Inventors: Jeewan Thakur, Basel (CH); Zhihui Qiu, Shanghai (CN)

(73) Assignee: Novartis AG (CH)

( * ) Notice: Subject to any disclaimer, the term of this patent is extended or adjusted under 35 U.S.C. 154(b) by 186 days.

(21) Appl. No.: 13/703,120

(22) PCT Filed: Jun. 29, 2011

(86) PCT No.: PCT/EP2011/060949
§ 371 (c)(1),
(2), (4) Date: Dec. 10, 2012

(87) PCT Pub. No.: WO2012/001074
PCT Pub. Date: Jan. 5, 2012

(65) Prior Publication Data
US 2013/0090344 A1   Apr. 11, 2013

(30) Foreign Application Priority Data
Jun. 30, 2010 (EP) .................................. 10168028

(51) Int. Cl.
*A61K 31/496* (2006.01)
*A61K 9/16* (2006.01)
*A61K 9/20* (2006.01)

(52) U.S. Cl.
CPC .......... *A61K 31/496* (2013.01); *A61K 9/1652* (2013.01); *A61K 9/2054* (2013.01)

(58) Field of Classification Search
CPC ............ A61K 9/2054; A61K 9/2077; A61K 9/2013; A61K 9/205; A61K 9/2866
See application file for complete search history.

(56) References Cited

U.S. PATENT DOCUMENTS

| | | | |
|---|---|---|---|
| 5,009,897 A | * | 4/1991 | Brinker ................ A61K 9/5073 424/469 |
| 2005/0740577 | | 11/2005 | Chou et al. |
| 2006/0172006 A1 | * | 8/2006 | Lenaerts et al. ............... 424/468 |
| 2007/0042034 A1 | * | 2/2007 | Zentner ................ A61K 9/2018 424/451 |
| 2008/0187582 A1 | * | 8/2008 | Guitard ................ A61K 31/404 424/464 |
| 2008/0293738 A1 | * | 11/2008 | Chou et al. ............... 514/253.07 |

FOREIGN PATENT DOCUMENTS

| | | | | |
|---|---|---|---|---|
| EP | 2108365 | | 10/2009 | |
| WO | WO 2006/127926 | | 11/2006 | |
| WO | 2008112509 A1 | | 9/2008 | |
| WO | 2009061446 A1 | | 5/2009 | |
| WO | WO 2009/115562 A2 | * | 9/2009 | .......... C07D 401/14 |
| WO | 2011128405 A1 | | 10/2011 | |

OTHER PUBLICATIONS

Reier (Avicel® PH Microcrystalline Cellulose, NF, Ph Eur., JP, BP, 2000, pp. 1-27).*
M.E. Aulton, "Farmacia. La ciencia del diseno de formas farmaceuticas" (Pharmacy. The science of design of pharmaceutical forms), Ed. Elsevier, 2nd edition, 2004, p. 146.
Galichet L.Y., "Cellulose, microcrystalline", Handbook of Pharmaceutical excipients, Fifth edition, pp. 132-135, 2006.

* cited by examiner

*Primary Examiner* — Mark V Stevens
(74) *Attorney, Agent, or Firm* — Gregory Ferraro

(57) ABSTRACT

A pharmaceutical composition for oral administration comprising 4-amino-5-fluoro-3-[6-(4-methylpiperazin-1-yl)-1H-benzimidazol-2-yl]-1H-quinolin-2-one monolactate monohydrate, a filler in an amount of 15 to 70% by weight, a disintegrant in an amount of less than 15% by weight, a glidant and/or a lubricant in an amount of 0.1 to 10% by weight wherein the amounts by weight are based on the total weight of the composition.

8 Claims, No Drawings

PHARMACEUTICAL COMPOSITIONS COMPRISING 4-AMINO-5-FLUORO-3-[6-(4-METHYLPIPERAZIN-1-Y1)-1H-BENZIMIDAZOL-2-Y1]-1H-QUINOLIN-2-ONE LACTATE MONOHYDRATE

The present invention relates to pharmaceutical compositions, in particular to compositions for administering 4-amino-5-fluoro-3-[6-(4-methylpiperazin-1-yl)-1H-benzimidazol-2-yl]-1H-quinolin-2-one or a tautomer thereof, a pharmaceutically acceptable salt or a hydrate or a solvate and to processes for manufacturing such compositions, for example the monohydrate form of the lactate salt thereof Published PCT application WO 2007/064719 describes pharmaceutical compositions of 4-amino-5-fluoro-3-[6-(4-methylpiperazin-1-yl)-1H-benzimidazol-2-yl]-1H-quinolin-2-one or a pharmaceutically acceptable salt or a hydrate or a solvate. In the embodiments of WO 2007/064719 the lactic acid salt is an anhydrous crystalline form such as form A. The anhydrous form has the disadvantages that it is not thermodynamically stable during the manufacturing process.

There remains a need for an economical and stable composition which overcomes the disadvantages described above. However the inventors have encountered the problem of providing a formulation comprising the active ingredient in a thermodynamically stable form, while keeping the same bioavailability as the formulation comprising the anhydrous form of the same active ingredient. The formulation according to the present invention is providing a pharmaceutical formulation with a higher drug load having a smaller size and is thus more user friendly.

The amounts of the excipients and active ingredients in the pharmaceutical compositions according to the invention as disclosed below are expressed in percentages by weight based on the total weight of the composition.

In one aspect the present invention provides a solid pharmaceutical composition for oral administration comprising 4-amino-5-fluoro-3-[6-(4-methylpiperazin-1-yl)-1H-benzimidazol-2-yl]-1H-quinolin-2-one or a pharmaceutically acceptable salt or a hydrate or a solvate in an amount of up to 70% by weight, e.g. of from 40% to 60 or 70%, a filler, for example microcrystalline cellulose, in an amount of 15 to 70% by weight, a disintegrant in an amount of less than 15% by weight, a glidant and/or a lubricant in an amount of 0.1 to 10% by weight, wherein the amounts by weight are based on the total weight of the composition.

The pharmaceutical composition may optionally comprise additional filler, e.g. mannitol which is present in an amount of 0.1 to 5% by weight wherein the amounts by weight are based on the total weight of the composition.

The pharmaceutical composition may further comprise a binder in an amount of 10 to 40% by weight.

In a further aspect the present invention provides a solid pharmaceutical composition for oral administration comprising 4-amino-5-fluoro-3-[6-(4-methylpiperazin-1-yl)-1H-benzimidazol-2-yl]-1H-quinolin-2-one or a pharmaceutically acceptable salt in an amount of up to 70% by weight, microcrystalline cellulose in an amount of 15 to 60% by weight, mannitol in an amount of 10 to 40% by weight, a disintegrant in an amount of less than 15% by weight, a glidant and/or a lubricant in an amount of 0.1 to 10% by weight, wherein the amounts by weight are based on the total weight of the composition.

In a further aspect the present invention provides a solid pharmaceutical composition for oral administration comprising 4-amino-5-fluoro-3-[6-(4-methylpiperazin-1-yl)-1H-benzimidazol-2-yl]-1H-quinolin-2-one or a pharmaceutically acceptable salt in an amount of up to 70% by weight, microcrystalline cellulose in an amount of 15 to 60% by weight, mannitol in an amount up to 10%, crospovidone in an amount up to 8%, a glidant and/or a lubricant in an amount of 0.1 to 10% by weight, wherein the amounts by weight are based on the total weight of the composition.

In the above embodiments the 4-amino-5-fluoro-3-[6-(4-methylpiperazin-1-yl)-1H-benzimidazol-2-yl]-1H-quinolin-2-one may be 4-amino-5-fluoro-3-[6-(4-methylpiperazin-1-yl)-1H-benzimidazol-2-yl]-1H-quinolin-2-one lactic acid monohydrate.

4-Amino-5-fluoro-3-[6-(4-methylpiperazin-1-yl)-1H-benzimidazol-2-yl]-1H-quinolin-2-one or a pharmaceutically acceptable salt or a hydrate or a solvate has the structure shown in Formula I:

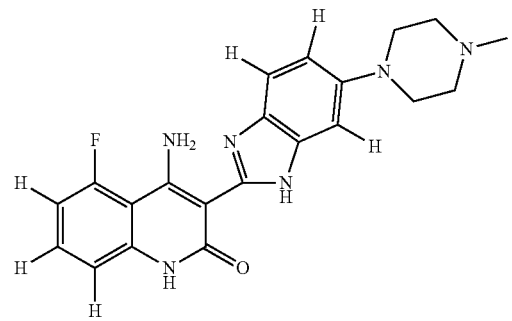 [SMILES: CN1CCN(c2ccc3nc(-c4c(N)c5c(F)cccc5[nH]c4=O)[nH]c3c2)CC1]

Preparation of this compound and its salts, including the mono-lactic acid salt, are described in U.S. Pat. Nos. 6,605,617, 6,774,237, 7,335,774, and 7,470,709, and in U.S. patent application Ser. Nos. 10/982,757, 10/982,543, and 10/706,328, and in the published PCT applications WO 2006/127926 and WO2009/115562, each of which is incorporated herein by reference in its entirety.

The lactate salt of the compound of Formula I exist in a variety of crystalline forms, including, e.g., an anhydrous form such as form A and the monohydrate form such as form $H_A$, also described as form B in WO 2006/127926.

In some specific embodiments, the lactic acid salt is a monohydrate crystalline form such as e.g., form $H_A$, also described as form B. Crystalline Form B of the lactic acid salt of a compound of Formula I has an X-ray powder diffraction pattern comprising characteristic peaks, in terms of 2θ, at about 17.6°, about 19.3° and about 26.0°. The X-ray powder diffraction pattern of Form B can further comprises characteristic peaks, in terms of 2θ, at about 23.3°, about 23.5° and about 28.2°. The X-ray powder diffraction pattern of Form B can further comprises characteristic peaks, in terms of 2θ, at about 11.9°, about 15.3°, about 16.1° and about 18.5°. The X-ray powder diffraction pattern of Form B can further comprises characteristic peaks, in terms of 2θ, at about 10.2° and about 12.9°. Crystalline Form B has an X-ray powder diffraction pattern comprising at least 3 characteristic peaks, in terms of 2θ, selected from at about 10.2, about 11.3, about 11.6, about 11.9, about 12.9, about 15.3, about 15.6, about 16.1, about 17.6, about 18.5, about 19.3, about 22.3, about 23.3, about 23.5, about 23.9, about 26.0, about 28.2, about 29.3, about 29.8, about 30.7, about 32.2, about 32.6, about 33.1 and about 34.3°. The X-ray diffraction diagram pattern of Form B is substantially as shown on FIG. 6 of WO 2006/127926.

The term "disintegrant" is understood to mean a substance or mixture of substances which facilitates disintegration of the composition after administration in order that the active ingredient be released from the composition as efficiently as possible to allow for its rapid dissolution (see e.g., "Remington's Pharmaceutical Science" 18th edition (1990), "The Theory and Practice of Industrial Pharmacy" Lachman et al. Lea & Febiger (1970)).

As disintegrant the composition of the present invention may comprise starches, clays, celluloses, alginates, gums, cross-linked polymers, e.g., cross-linked polyvinyl pyrrolidone or crospovidone, e.g., Kollidon from BASF, e.g., Polyplasdone from International Speciality Products (Wayne, N.J.), e.g. Crospovidone XL, cross-linked sodium carboxymethylcellulose or croscarmellose sodium, e.g., AC-DI-SOL from FMC, cross-linked calcium carboxymethylcellulose, soy polysaccharides and guar gum. The disintegrant may be present in an amount from about 0.1% to about 10% by weight of the composition. In one embodiment the disintegrant is present in an amount from about 4% to about 8% by weight of the composition or in an amount of more than 4% to 8%, e.g. 5% to 8% by weight of the composition, e.g. 6% to 8%, e.g. 6.5 to 7.5%.

The disintegrant may be crospovidone, for example Crospovidone XL, which is preferably water insoluble. Ideally the disintegrant rapidly exhibits high capillary or pronounced hydration capacity with little tendency to gel formation. According to the present invention, crospovidone, e.g. Crospovidone XL, is present in an amount of more than 4% to 8%, e.g. 5% to 8% by weight, e.g. 6% to 8%, e.g. 6.5% to 7.5%, wherein the amounts by weight are based on the total weight of the composition.

The composition of the present invention may further comprise one or more fillers. Examples of pharmaceutically acceptable fillers include, but are not limited to, confectioner's sugar, compressible sugar, dextrates, dextrin, dextrose, lactose, mannitol, microcrystalline cellulose, powdered cellulose, sorbitol, sucrose, dicalcium phosphate, starch, pregelatinated starch and talc, in one embodiment of the invention fillers are microcrystalline cellulose, e.g. MCC 102, MCC 105, MCC 112, MCC 200 or/and mannitol. The filler may be present in an amount from about 15% to about 60% by weight, e.g. one or more filler are present in an amount of 30% to 60%, e.g. 35% to 60%, e.g. 38 to 50% by weight wherein the amounts by weight are based on the total weight of the composition. The composition of the invention comprises one or more filler selected from microcrystalline cellulose, e.g. MCC102, MCC 105, MCC 200 and mannitol in a total amount of filler of 30 to 60%, e.g. 32 to 50%, e.g. 32 to 46% in weight wherein the amounts by weight are based on the total weight of the composition.

The composition of the invention may further comprise a binder. Examples of pharmaceutically acceptable binders include, but are not limited to, starches, celluloses and derivatives thereof, e.g., microcrystalline cellulose, e.g., hydroxypropyl cellulose, e.g., hydroxyethyl cellulose, e.g., hydroxypropylmethyl cellulose, sucrose, dextrose, corn syrup, polysaccharides, gelatin, polyvinyl pyrrolidone, copovidone, e.g., Kollidon VA64 from BASF. The binder may be present in an amount from about 0% to about 50%, e.g., 10-40% weight by weight of the composition.

The composition of the present invention may further comprise a lubricant or a glidant. Examples of pharmaceutically acceptable lubricants and pharmaceutically acceptable glidants include, but are not limited to, colloidal silica, e.g., colloidal silicon dioxide, magnesium trisilicate, starches, talc, tribasic calcium phosphate, magnesium stearate, aluminum stearate, calcium stearate, magnesium carbonate, magnesium oxide, polyethylene glycol, powdered cellulose and microcrystalline cellulose. The lubricant, e.g., may be present in an amount from about 0.1% to about 5% by weight of the composition; whereas, the glidant, e.g., may be present in an amount from about 0.1% to about 10% by weight by weight of the composition, e.g. silicon dioxide may be present in an amount of from 0.5 to 2%; magnesium stearate may be present in an amount of from 1 to 4% by weight by weight of the composition.

Other excipients disclosed in the literature, as for instance in Fiedler's "Lexicon der Hilfstoffe", 4th Edition, ECV Aulendorf 1996 and "Handbook of Pharmaceutical Excipients" Wade and Weller Ed.(1994), the contents of which are incorporated herein by reference, may be used in the pharmaceutical compositions according to the invention.

Mannitol may be used as a filler. Mannitol is a hydrophilic component. Therefore if mannitol comes in contact with water, e.g. gastric juice solubilizes it quickly leaving a porous structure which water can penetrate easily. This has the advantage that it increases the dissolution rate which is a key factor for the immediate release pharmaceutical composition of the present invention.

In a further aspect the present invention provides a process for the production of the compositions of the invention. The compositions of the invention may be prepared by working up active agent with excipients. The processes provided are dry granulation processes.

The dry granulation process provides advantages overcoming drug substance properties such as sticking of the drug substance and excipients during the manufacturing process. Generally, the composition of the invention may be obtained by preparing a mixture of 4-amino-5-fluoro-3-[6-(4-methylpiperazin-1-yl)-1H-benzimidazol-2-yl]-1H-quinolin-2-one, with the above mentioned pharmaceutical excipients, such as filler, additional filler, disintegrant, glidant, lubricant etc. by standard methods, processing the mixture by roller compaction to provide yield a milled granulate and processing the milled granulate into capsules or tablets by standard methods.

Process A

The composition of the invention may be obtained by
(i) Preparing a mixture of 4-amino-5-fluoro-3-[6-(4-methylpiperazin-1-yl)-1H-benzimidazol-2-yl]-1H-quinolin-2-one, one or more filler, e.g. filler, additional filler, disintegrant and glidant
(ii) Sieving the mixture of step (i)
(iii) Lubricating the mixture of step (ii) with a lubricant
(iv) Processing the mixture of step (iii) by roller compaction
(v) Blending milled granulate of step (iv) with disintegrant and glidant
(vi) Lubricating with a lubricant
(vii) Encapsulation of the mixture of step (vi)

Process B

The composition of the invention may be obtained by
(i) Preparing a mixture of 4-amino-5-fluoro-3-[6-(4-methylpiperazin-1-yl)-1H-benzimidazol-2-yl]-1H-quinolin-2-one or a pharmaceutically acceptable salt or a hydrate or a solvate, filler, disintegrant and lubricant
(ii) Sieving the mixture
(iii) Adding lubricant
(iv) Processing the mixture of step iii) by roller compaction
(v) Blending milled granulate of step (iv) with glidant, filler and disintegrant and mixing
(vi) Lubricating with a lubricant
(vii) Forming tablets by compression
(viii) Optionally the tablets may be coated The resulting powder blends of step vii) are compressed on either a single punch press (Korsh EKO), 6 station-rotary press (Korsh PH106), 17 station-rotary press (Korsh PH 230) or 43 station-rotary press (Fette PT2090).

The composition of the invention may be formulated as a gelatine capsule such as a hard gelatine capsule. The hard gelatin capsule, also known as a dry-filled capsule, is composed of two sections, one slipping over the other, thus completely surrounding (encapsulating) the drug formulation.

The composition of the present invention may be formulated as a tablet.

In one embodiment, the present invention provides tablet compositions with an average hardness of e.g. from 60 to 250 N, preferably from 110 N to 190 N.

The particles or granules obtained by the manufacturing processes B as described above, or the tablet, may be coated with a non-functional coating as known in the art, for example hydroxypropylmethyl cellulose (HPMC) coating. Suitable coatings may comprise cellulose or derivatives based coatings, e.g., ethylcellulose, e.g. hydroxypropylmethylcellulose, e.g., carboxymethylcellulose, e.g., hydroxyethylcellulose, e.g., cellulose acetate, e.g., cellulose acetate phthalate, e.g., hydroxypropylmethyl cellulose succinate, methylacrylate or polymethylacrylate, a polymethacrylic acid polymer, e.g., Eudragit The utility of the pharmaceutical compositions of the present invention may be observed in standard clinical tests, including bioavailability tests, in, for example, known indications of drug dosages giving therapeutically effective blood levels of the therapeutic compound; for example using dosages in the range of 25-1000 mg of therapeutic compound per day or alternative dosing regimens for a 75 kg mammal, e.g., adult human and in standard animal models.

Depending on species, age, individual condition, and the clinical picture in question, effective doses for example weekly doses of about 500 to 4000 mg, of 4-amino-5-fluoro-3-[6-(4-methylpiperazin-1-yl)-1H-benzimidazol-2-yl]-1H-quinolin-2-one or a pharmaceutically acceptable salt or a hydrate or a solvate are administered to a human.

The invention pertains to a pharmaceutical composition comprising 4-amino-5-fluoro-3-[6-(4-methylpiperazin-1-yl)-1H-benzimidazol-2-yl]-1H-quinolin-2-one monohydrate mono lactate 40 to 65% by weight, e.g. 50%, one or more filler, for example, microcrystalline cellulose 102, 105, and/or 200, for example MCC 102 and MCC200 or MCC105 and MCC200, crospovidone, e.g. crospovidone XL, in an amount of 5 to 7% by weight, silicon dioxide 1 to 1.5% by weight, magnesium stearate in an amount of 2 to 3% by weight by weight of the total weight of the formulation A pharmaceutical composition according to the invention comprising in the intragranular phase 4-amino-5-fluoro-3-[6-(4-methylpiperazin-1-yl)-1H-benzimidazol-2-yl]-1H-quinolin-2-one monohydrate monolactate 40 to 65% by weight, e.g. 50%, one or more filler, for example microcrystalline cellulose or microcrystalline cellulose and mannitol, for example microcrystalline cellulose 102, 105 or mixture thereof, e.g. in an amount of 30 to 50% by weight, crospovidone, e.g. crospovidone XL, in an amount of 2 to 7% by weight, silicon dioxide 0.5 to 1% by weight, magnesium stearate in an amount of 0.1 to 1% by weight, and in the extragranular phase silicon dioxide for example in an amount of 0.2 to 1% magnesium stearate in an amount of 1 to 3% by weight, crospovidone, e.g. crospovidone XL, in an amount of 1 to 5% by weight by weight of the total weight of the formulation.

When the composition is a tablet the extragranular phase comprises a filler, e.g. microcrystalline cellulose in an amount of 3 to 7% by weight by weight of the total weight of the formulation.

A tablet composition according to the present invention comprises in the intragranular phase 4-amino-5-fluoro-3-[6-(4-methylpiperazin-1-yl)-1H-benzimidazol-2-yl]-1H-quinolin-2-one monohydrate monolactate 45 to 65%, e.g. 50% by weight, one or more filler, for example microcrystalline cellulose, for example microcrystalline cellulose 102, 105 or mixture thereof, e.g. in an amount of 30 to 50% by weight, crospovidone, e.g. crospovidone XL, in an amount of 2 to 6% by weight, silicon dioxide 0.5 to 1% by weight, magnesium stearate in an amount of 0.1 to 0.5% by weight, and in the extragranular phase silicon dioxide for example in an amount of 0.2 to 1% by weight, magnesium stearate in an amount of 1 to 3% by weight, crospovidone, e.g. crospovidone XL, in an amount of 3 to 5%, e.g. 4 to 5% by weight, a filler, for example microcrystalline cellulose, for example MCC 200, for example in an amount of 3% to 5% by weight by weight by weight of the total weight of the formulation. The tablets according to the present invention are film-coated tablets.

A capsule composition according to the present invention comprises in the intragranular phase 4-amino-5-fluoro-3-[6-(4-methylpiperazin-1-yl)-1H-benzimidazol-2-yl]-1H-quinolin-2-one monohydrate monolactate 30 to 50% by weight, e.g. 40 to 42% by weight, one or more filler, for example microcrystalline cellulose, for example microcrystalline cellulose 102, 105, 200, mannitol or mixture thereof, e.g. in an amount of 30 to 50% by weight, crospovidone, e.g. crospovidone XL, in an amount of 4 to 6% by weight, silicon dioxide 0.5 to 1% by weight, magnesium stearate in an amount of 0.1 to 0.5% by weight, and in the extragranular phase silicon dioxide for example in an amount of 0.2 to 1% magnesium stearate by weight in an amount of 1 to 3% by weight, crospovidone, e.g. crospovidone XL, in an amount of 3 to 5%, by weight e.g. 4 to 5% by weight, a filler, for example microcrystalline cellulose, for example MCC 200, for example in an amount of 3% to 5% by weight wherein the amounts by weight are based on the total weight of the composition. The tablet is or can be coated, e.g. film-coated.

The invention pertains to a pharmaceutical composition for oral administration comprising 4-amino-5-fluoro-3-[6-(4-methylpiperazin-1-yl)-1H-benzimidazol-2-yl]-1H-quinolin-2-one or a pharmaceutically acceptable salt or a hydrate or a solvate in an amount of up to 45% by weight, a filler in an amount of 15 to 70% by weight, a disintegrant in an amount of less than 15% by weight, a glidant and/or a lubricant in an amount of 0.1 to 10% by weight, wherein the amounts by weight are based on the total weight of the composition, said composition can further comprise an additional filler, that can be mannitol, for example in an amount of 0.1 to 5% in weight by weight of the total weight of the composition.

The invention also pertains to a pharmaceutical composition for oral administration comprising 4-amino-5-fluoro-3-[6-(4-methylpiperazin-1-yl)-1H-benzimidazol-2-yl]-1H-quinolin-2-one or a pharmaceutically acceptable salt in an amount of up to 45% by weight, microcrystalline cellulose in an amount of 15 to 60% by weight, mannitol in an amount of 10 to 40% by weight, a disintegrant in an amount of less than 15% by weight, a glidant and/or a lubricant in an amount of 0.1 to 10% by weight, wherein the amounts by weight are based on the total weight of the composition, for example, wherein the disintegrant is crospovidone and/or wherein the glidant is magnesium stearate.

Following is a non-limiting description by way of examples.

According to the below examples and to the specification above, the capsule or tablet dose would refer to the weight of 4-amino-5-fluoro-3-[6-(4-methylpiperazin-1-yl)-1H-benzimidazol-2-yl]-1H-quinolin-2-one lactic acid present in the formulation, for example a 100 mg tablet comprises 100 mg of 4-amino-5-fluoro-3-[6-(4-methylpiperazin-1-yl)-1H-benzimidazol-2-yl]-1H-quinolin-2-one lactic acid so 128 mg of 4-amino-5-fluoro-3-[6-(4-methylpiperazin-1-yl)-1H-benzimidazol-2-yl]-1H-quinolin-2-one lactic acid monolactate monohydrate. The percentages in the composition as detailed below are expressed in weight by weight based on the total weight of the tablet and in case of the active ingredient the percentage corresponds to the percentage of the monohydrate monolactate salt thereof present in the composition.

EXAMPLE 1

A 100 mg capsule of 4-amino-5-fluoro-3-[6-(4-methylpiperazin-1-yl)-1H-benzimidazol-2-yl]-1H-quinolin-2-one lactic acid monohydrate (Compound X) is prepared using the dry granulation method

| Component | % w/w |
|---|---|
| Compound X | 41.29 |
| Microcrystalline cellulose | 45.32 |
| Mannitol | 3.23 |
| Crospovidone | 7.42 |
| Silicon dioxide, e.g. Aerosil | 0.97 |
| Magnesium stearate | 1.78 |

A mixture of compound X, microcrystalline cellulose, crospovidone, mannitol and Aerosil is formed. This mixture is sieved and lubricated with magnesium stearate. The mixture is processed by roller compaction. The resulting milled granulate is blended with crospovidone and Aerosil. The mixture is lubricated with magnesium stearate and the mixture is encapsulated.

EXAMPLE 2

A 25 mg capsule of 4-amino-5-fluoro-3-[6-(4-methylpiperazin-1-yl)-1H-benzimidazol-2-yl]-1H-quinolin-2-one lactic acid monohydrate (compound X) is prepared using the dry granulation method

| Component | % w/w | |
|---|---|---|
| Compound X | 41.29 | 41.13 |
| Microcrystalline cellulose | 45.32 | 45.5 |
| Mannitol | 3.23 | 3.22 |
| Crospovidone | 7.42 | 7.49 |
| Silicon dioxide, e.g. Aerosil | 0.97 | 0.96 |
| Magnesium stearate | 1.78 | 1.77 |

A mixture of compound X, microcrystalline cellulose, crospovidone, mannitol and Aerosil is formed. This mixture is sieved and lubricated with magnesium stearate. The mixture is processed by roller compaction. The resulting milled granulate is blended with crospovidone and Aerosil. The mixture is lubricated with magnesium stearate and the mixture is encapsulated.

EXAMPLE 3

A 100 mg tablet of 4-amino-5-fluoro-3-[6-(4-methylpiperazin-1-yl)-1H-benzimidazol-2-yl]-1H-quinolin-2-one lactic acid monohydrate (compound X) is prepared using the dry granulation method

| Component | % w/w |
|---|---|
| Compound X | 49.80 |
| Microcrystalline cellulose | 41.50 |
| Crospovidone | 5.0 |
| Silicon dioxide, e.g Aerosil | 1.2 |
| Magnesium stearate | 2.5 |

A mixture of compound X, microcrystalline cellulose, crospovidone and Aerosil is formed. This mixture is sieved and lubricated with magnesium stearate. The mixture is processed by roller compaction. The resulting milled granulate is blended with Aerosil and crospovidone. This mixture is lubricated with magnesium stearate. The tablets are formed by compression.

EXAMPLE 4

A 250 mg tablet of 4-amino-5-fluoro-3-[6-(4-methylpiperazin-1-yl)-1H-benzimidazol-2-yl]-1H-quinolin-2-one lactic acid monohydrate (compound X) is prepared using the dry granulation method

| Component | % w/w |
|---|---|
| Compound X | 49.80 |
| Microcrystalline cellulose | 41.50 |
| Crospovidone | 5.0 |
| Silicon dioxide, e.g Aerosil | 1.2 |
| Magnesium stearate | 2.5 |

A mixture of compound X, microcrystalline cellulose, crospovidone and Aerosil is formed. This mixture is sieved and lubricated with magnesium stearate. The mixture is processed by roller compaction. The resulting milled granulate is blended with Aerosil and crospovidone. This mixture is lubricated with magnesium stearate. The tablets are formed by compression.

EXAMPLE 5

A 25 mg tablet of 4-amino-5-fluoro-3-[6-(4-methylpiperazin-1-yl)-1H-benzimidazol-2-yl]-1H-quinolin-2-one lactic acid monohydrate (compound X) is prepared using the dry granulation method

| Component | % w/w |
|---|---|
| Compound X | 50.0 |
| Microcrystalline cellulose | 30.7 |
| Copovidone, e.g. Kollidon VA64 | 8.0 |
| Crospovidone | 7.0 |
| Silicon dioxide, e.g Aerosil | 1.0 |
| Magnesium stearate | 2.4 |

A mixture of compound X, microcrystalline cellulose, crospovidone, Kollidon VA64 and Aerosil is formed. This mixture is sieved and lubricated with magnesium stearate. The mixture is processed by roller compaction. The resulting milled granulate is blended with Aerosil and crospovidone.

This mixture is lubricated with magnesium stearate. The tablets are formed by compression.

EXAMPLE 6

Capsules and tablets provide a fast release of the active substance. Dissolution rates are measured in standard dissolution tests, e.g. effected by use of the apparatus 2 (Rotary Paddle) of the USP at 37 degree Celsius in dissolution rate medium A (pH approximately 1.5; 0.04 Molar HCl+2 g/lit NaCl) and in dissolution rate medium B (pH 4.5 acetate buffer) at a stirring rate of 50 rpm and based on the mean of 6 or more e.g., 12 dosage forms. 100 mg capsule dissolution rates for n=6:

| Time (min) | Medium A % released | Medium B % released |
|---|---|---|
| 10 | 82 | 65 |
| 20 | 89 | 76 |
| 30 | 92 | 77 |
| 45 | 94 | 86 |
| 60 | 97 | 88 |

25 mg capsule dissolution rates for n=6

| Time (min) | Medium A % released | Medium B % released |
|---|---|---|
| 10 | 84 | 59 |
| 20 | 94 | 72 |
| 30 | 99 | 76 |
| 45 | 100 | 81 |
| 60 | 100 | 84 |

100 mg tablet dissolution rates for n=6

| Time (min) | Medium A % released | Medium B % released |
|---|---|---|
| 10 | 90 | 80 |
| 15 | 99 | 88 |
| 20 | 100 | 89 |
| 30 | 101 | 92 |
| 45 | 102 | 94 |
| 60 | 102 | 96 |

250 mg tablet dissolution rates for n=12 for pH 1.5 and n=6 for pH 4.5

| Time (min) | Medium A % released | Medium B % released |
|---|---|---|
| 10 | 91 | 87 |
| 15 | 96 | 91 |
| 20 | 97 | 94 |
| 30 | 98 | 95 |
| 45 | 99 | 97 |
| 60 | 100 | 97 |

25 mg tablet dissolution rates for n=6

| Time (min) | Medium A % released | Medium B % released |
|---|---|---|
| 10 | 99 | 90 |
| 20 | 99 | 94 |
| 30 | 99 | 95 |
| 45 | 99 | 93 |
| 60 | 99 | 94 |
| 75 | 99 | 94 |

EXAMPLE 7

Bioavailability Study

The compositions of the invention (the tablet and the capsule) comprising 4-amino-5-fluoro-3-[6-(4-methylpiperazin-1-yl)-1H-benzimidazol-2-yl]-1H-quinolin-2-one lactic acid monohydrate have been tested and compared with the formulation described in WO 2007/064719 using an anhydrous form of the drug substance (formulation Y) in a dog study. The pharmacokinetic parameters Cmax and AUC have been measured. The study has been done with 6 dogs for each formulation using 25 mg formulations. The parameters Cmax and AUC have been found to be comparable.

Cmax (ng/ml)

|  | Formulation Y | Capsule | Tablet |
|---|---|---|---|
| Lower 95% CI | 7.6 | 6.2 | 5.2 |
| Mean | 11 | 10.4 | 9.4 |
| Upper 95% CI | 14.4 | 14.6 | 13.5 |

AUC-12 hours

|  | Formulation Y | Capsule | Tablet |
|---|---|---|---|
| Lower 95% CI | 48.3 | 39.7 | 32 |
| Mean | 67.7 | 67.5 | 62.4 |
| Upper 95% CI | 87 | 95.3 | 92.8 |

EXAMPLE 8

Assessment of bioavailability of the capsule comprising anhydrous monolactate of 4-amino-5-fluoro-3-[6-(4-methylpiperazin-1-yl)-1H-benzimidazol-2-yl]-1H-quinolin-2-one versus tablets comprising monohydrous monolactate of 4-amino-5-fluoro-3-[6-(4-methylpiperazin-1-yl)-1H-benzimidazol-2-yl]-1H-quinolin-2-one A total of 21 subjects were randomized to the 2 treatment sequences Day 1: 500 mg as tablet or 500 mg as capsule, then rest Day 2 until day 8 and Day 9 like Day 1. Out of the total randomized subjects, a total of 17 (81%) received both of the planned doses at 500 mg during cycle 1, and provided evaluable pharmacokinetic data, and included in this analysis.

A formal statistical analysis was performed to estimate the relative bioavailability of the capsule formulation of 4-amino-5-fluoro-3-[6-(4-methylpiperazin-1-yl)-1H-benzimidazol-2-yl]-1H-quinolin-2-one according to the invention as compared to the capsule formulation according to US2008/0293738 A1, capsule composition 13. A linear mixed effects model was fitted to the log-transformed PK parameters ($AUC_{0\text{-}tlast}$, $AUC_{0\text{-}\infty}$, and $C_{max}$). Included in the model were treatment, period, and sequence as fixed factors and subjects nested within sequences as a random factor.

For the bioavailability analysis, the capsule formulation according to the present invention was the test and the intact capsule formulation was the reference to US2008/0293738 A1. The two-sided 90% CI for the least square means of the difference (test–reference) on the log-scale was calculated. This was anti-logged to obtain the point estimates and the 90% confidence interval for the ratio of the geometric means on the untransformed scale.

The summary of the statistical analysis (adjusted geo-means, the geo-mean ratio and the 90% confidence interval) for the PK parameters ($C_{max}$, $AUC_{0-tlast}$, $AUC_{0-\infty}$), and the median along with the minimum and the maximum range for $T_{max}$ is presented in the below table, by treatment group.

The geometric mean ratio for the primary PK parameters and 90% CI comparing (500 mg) tablet versus (500 mg) capsule are listed as follows:

$AUC_{inf}$(hr×ng/mL): 0.88 (0.72 to 1.07)
$AUC_{0-tlast}$(hr×ng/mL): 0.96 (0.89 to 1.04)
$C_{max}$(ng/mL): 0.99 (0.91 to 1.08)

The summary of the statistical analysis (adjusted geo-means, the geo-mean ratio and the 90% confidence interval) for the PK parameters ($C_{max}$, $AUC_{0-tlast}$, $AUC_{0-\infty}$), and the median along with the minimum and the maximum range for $T_{max}$ is presented in the below table by treatment group.

8.2 Assessment of bioavailability of the capsule comprising anhydrous monolactate of 4-amino-5-fluoro-3-[6-(4-methylpiperazin-1-yl)-1H-benzimidazol-2-yl]-1H-quinolin-2-one versus capsules comprising monohydrous monolactate of 4-amino-5-fluoro-3-[6-(4-methylpiperazin-1-yl)-1H-benzimidazol-2-yl]-1H-quinolin-2-one (Compound X in the below examples).

Study Design

A total of 20 eligible patients have been enrolled and randomly assigned into 1 of 2 treatment sequences as presented in the below table.

|  | Period 1 | | Period 2 |
|---|---|---|---|
| Cycle 1 | Day 1 | Days 2-8 | Day 9 |
| Sequence 1 | 500 mg (anhydrous caps) | Rest | 500 mg (monohydrous caps) |
| Sequence 2 | 500 mg (monohydrous caps) | Rest | 500 mg (anhydrous caps)) |

Ratio of geometric means with (90% CI) of Compound X primary PK parameters (Arm 1) PK set

| PK Parameter (unit) | Treatment | n* | Adjusted Geo-mean | Comparison | Treatment Comparison Geo-mean Ratio | 90% CI Lower | Upper |
|---|---|---|---|---|---|---|---|
| AUC(0-inf) (ng * hr/mL) | CSF | 6 | 6402.35 | | | | |
| | FMI | 8 | 5604.93 | FMI:CSF | 0.88 | 0.72 | 1.07 |
| AUC(0-tlast) (ng * hr/mL) | CSF | 17 | 4738.24 | | | | |
| | FMI | 17 | 4568.27 | FMI:CSF | 0.96 | 0.89 | 1.04 |
| Cmax (ng/mL) | CSF | 17 | 192.33 | | | | |
| | FMI | 17 | 190.47 | FMI:CSF | 0.99 | 0.91 | 1.08 |
| Tmax (hr) | CSF | 17 | 7.00 | | | | |
| | FMI | 17 | 7.00 | FMI-CSF | 0.00 | −4.00 | 1.95 |

CSF corresponds to capsules, FMI corresponds to tablets.

The conclusion of this study is that the tablet according to the present invention provides the active ingredient with a bioavailability equivalent to the one of the capsule according to US2008/0293738 A1, capsule composition 13, this result was not foreseeable.

The summary of the statistical analysis (adjusted geo-means, the geo-mean ratio and the 90% confidence interval) for the PK parameters ($C_{max}$, $AUC_{0-tlast}$, $AUC_{0-\infty}$), and the median along with the minimum and the maximum range for $T_{max}$ is presented in the table below, by treatment group.

| PK Parameter (unit) | Treatment | n* | Adjusted Geo-mean | Comparison(s) | Treatment Comparison Geo-mean ratio | 90% CI Lower | Upper |
|---|---|---|---|---|---|---|---|
| AUC(0-inf) (h · ng/mL) | CSF | 16 | 7127.47 | | | | |
| | FMI | 16 | 6286.50 | FMI/CSF | 0.88 | 0.79 | 0.98 |
| AUC(0-tlast) (h · ng/mL) | CSF | 16 | 5577.41 | | | | |
| | FMI | 16 | 4886.40 | FMI/CSF | 0.88 | 0.80 | 0.95 |
| Cmax (ng/mL) | CSF | 16 | 226.29 | | | | |
| | FMI | 16 | 213.44 | FMI/CSF | 0.94 | 0.85 | 1.04 |
| Tmax (h) | CSF | 16 | 6.00 | | | | |
| | FMI | 16 | 5.04 | FMI/CSF | | 0.00 | 2.00 |

CSF corresponds to capsules comprising anhydrous monolactate of 4-amino-5-fluoro-3-[6-(4-methylpiperazin-1-yl)-1H-benzimidazol-2-yl]-1H-quinolin-2-one, FMI corresponds to tablets monohydrate monolactate of 4-amino-5-fluoro-3-[6-(4-methylpiperazin-1-yl)-1H-benzimidazol-2-yl]-1H-quinolin-2-one.

The geometric mean ratio for the primary PK parameters and 90% CI comparing FMI (500 mg) versus CSF (500 mg) are as follows:

$AUC_{inf}$(hr××ng/mL): 0.88 (0.79 to 0.98)
$AUC_{0\text{-}tlast}$(hr×ng/mL): 0.88 (0.80 to 0.95)
$C_{max}$(ng/mL): 0.94 (0.85 to 1.04)

Inter-individual variability for all the above PK parameters was similar between the capsule according to US2008/0293738 A1, capsule composition 13 and the capsule according to the present invention. The PK results demonstrate that the two capsules have comparable bioavailability.

EXAMPLE 9

The following blend made of Compound X active ingredient 36.6%, MCC 200 40%, mannitol 10%, hydroxypropylcellulose 4%, croscarmellose sodium 6%, silicon dioxide 0.86%, magnesium stearate 2.57% was compressed into tablets. Besides the slow release profile, the tablet parameters mainly friability were unsatisfactory.

EXAMPLE 9bis

The following blend was prepared active ingredient 36.6%, MCC 112 42.6%, MCC 200 4.8%, PVPK30 4.9%, Crospovidone XL 8%, Silicon dioxide 1.14%, Magnesium stearate 2% and compressed into tablets. The dissolution release profile was faster than for example 8 however the tablets failed the friability test, despite in presence of a binder.

EXAMPLE 10

Tablets According have the Following Composition

| Composition | % w/w |
| --- | --- |
| Intra granular | |
| Compound X | 44.3 |
| Microcrystalline cellulose (MCC105) | 40.1 |
| Povidone K30 | 4.8 |
| Crospovidone XL | 2.8 |
| Colloidal Silicon Dioxide | 0.7 |
| Magnesium stearate | 0.7 |
| Extra granular | |
| Magnesium stearate | 1.4 |
| Colloidal Silicon Dioxide | 0.35 |
| Crospovidone XL | 4.8 |

Tablets were prepared by roller compaction and the dissolution time and friability results were satisfactory.

The corresponding tablet comprising MCC 101 or MCC 112 instead of MCC 105 and less crospovidone showed sticking to the roller and a lower mean dissolution release in acetate buffer pH4.5 and in SGF at 10 minutes. Therefore, surprisingly in view of the test results, MCC 101 seems to lead to variations with respect to the compaction process in the manufacture of the tablet according to the present invention.

EXAMPLE 11

A formulation similar to the one of Example 10 was prepared comprising 63% of active ingredient and a corresponding decrease in MCC 105 and increase in the other excipients. The formulation gave satisfactory results from the friability and DT tests, while the dissolution in pH4.5 was low.

EXAMPLE 12

A similar formulation as in Example 10 and 11 was prepared comprising 11.3% MCC 105 and pregelatinized starch 15%, for example Starch 1500, instead of MCC 105 and PVPK30. Tablets failed the friability test, and dissolution was slow in both media even though disintegration time was within 10 min, surprisingly showing that pregelatinized starch might not be appropriate in association with the monohydrate form of the active ingredient.

EXAMPLE 13

A similar formulation as example 10 with a drug load of 55% fulfilled both the friability and dissolution tests, despite the disintegration time was 15 min.

EXAMPLE 14 corresponds to a formulation similar to the one of Example 13 with a drug load of 55% wherein Povidone K30 is replaced by Copovidone, e.g. Kollidon VA64 Fine, 8% and the amount of MCC 105 reduced accordingly. The friability was increased as compared to Example 13 and the dissolution rate dropped by 10%, especially at 10 min time point. Surprisingly the dissolution rate was fast despite the disintegration time between 16 to 18 min.

EXAMPLE 15

The formulation has a drug load of 50%, Kollidon VA64 Fine 8% and the amount of the other excipients. Sticking was observed on the die rollers during roller compaction.

In summary of Examples 14 and 15, Copovidone as excipient did not improve the properties of the formulation contrary to expectations, in terms of friability.

EXAMPLE 16

| Intra granular | |
| --- | --- |
| Compound X | 50 |
| Microcrystalline cellulose (MCC105) | 40.7 |
| Crospovidone XL | 1.1 |
| Colloidal Silicon Dioxide | 0.7 |
| Magnesium stearate | 0 or 0.5 |
| Extra granular | |
| Microcrystalline cellulose (MCC200) | 5.0 |
| Colloidal Silicon Dioxide | 0.34 |
| Crosprovidone XL | 1.1 |
| Magnesium stearate | 1.1 |
| Total in % weight/weight | 100.0 |

This formulation exhibited good processability with no sticking however picking was observed that could be avoided by adding 0.5% of magnesium stearate in the intragranular phase or increasing the compression force.

In an alternative, the amount of magnesium stearate in the extra granular phase is increased by 0.5% when magnesium stearate is present in the intragranular phase and process was discontinued due to sticking issues.

EXAMPLE 17

This formulation corresponds to the formulation of Example 16 where Crospovidone is present in a total of 4%, MCC200 is absent from the extragranular phase and Copovidone is present in an amount of 4%. Sticking on the roller was observed as well as poor dissolution release and too slow disintegration time.

This data confirms that Copovidone might not be used in the formulation and could prevent good release profile.

EXAMPLE 18

| Formulation number | A | B | C |
|---|---|---|---|
| Intra granular | | | |
| Compound X | 50 | 49.8 | 50 |
| Microcrystalline cellulose (MCC105) | 36.3 | — | 31.6 |
| Microcrystalline cellulose (MCC102) | — | 34.8 | — |
| Crospovidone XL | 2.0 | 2.7 | 3 |
| Colloidal Silicon Dioxide | 0.7 | 0.7 | 0.7 |
| Magnesium stearate | 1.0 | 0.25 | 0.5 |
| Extra granular | | | |
| Microcrystalline cellulose (MCC200) | 5.0 | 5.0 | 7.5 |
| Colloidal Silicon Dioxide | 0.5 | 0.5 | 0.5 |
| Crospovidone XL | 3.0 | 4.1 | 4.5 |
| Magnesium stearate | 1.5 | 2.0 | 1.75 |
| Total % weight/weight | 100.0 | 100.0 | 100.0 |

These formulations successfully complied with all tests performed and no issue occurred during the manufacturing process.

EXAMPLE 20

Capsules comprising the monolactate monohydrate form of Compound X should have a release profile as close as possible to the one of the capsules comprising Compound X in the anhydrous form. The composition of the formulation also needs to allow running a robust process. Finally the formulation shall meet the standard of stability.

Surprisingly it was found that the use of Croscarmellose sodium was not suitable as there was an interaction between Compound X monohydrate form and this excipient at pH4.5 which prevents to achieve a satisfactory release profile, i.e. a release profile of about 75 to 80% in a pH4.5 media for 60 min. This was not expected.

Sticking on the rollers during the process was to be solved. Defective capsules were obtained because of the overfilling of Size 1 capsules during the encapsulation process so this problem was addressed by reducing the full weight.

Hydroxypropyl cellulose was tested as a filler and the dissolution release was slower. Mannitol up to 10% was included and this had no negative impact on the dissolution release. Surprisingly MCC 101 was found to lead to a poorer release profile of the capsule formulation and this was unexpected for the same reasons as mentioned above, namely that MCC 101 was mentioned in the preparation of the formulation according to WO2007/064719.

| Formulation number | A | B | C | D | E |
|---|---|---|---|---|---|
| Intra granular | | | | | |
| Compound X | 41.13 | 41.29 | 41.29 | 41.29 | 41.29 |
| Microcrystalline cellulose (MCC102) | 45.5 | 45.32 | — | 46.29 | 46.93 |
| Microcrystalline cellulose (MCC200) | — | — | 39.03 | — | — |
| Mannitol 200 SD | 3.22 | 3.23 | 10.32 | 3.23 | 3.23 |
| Crospovidone XL | 5.81 | 5.81 | 4.52 | 5.16 | 4.84 |
| Colloidal Silicon Dioxide | 0.64 | 0.65 | 0.65 | 0.65 | 0.65 |
| Magnesium stearate | 0.64 | 0.65 | 0.65 | 0.65 | 0.65 |
| Extra granular | | | | | |
| Colloidal Silicon Dioxide | 0.32 | 0.32 | 0.32 | 0.32 | 0.32 |
| Crospovidone XL | 1.61 | 1.61 | 2.26 | 1.29 | 0.97 |
| Magnesium stearate | 1.13 | 1.13 | 0.97 | 1.13 | 1.13 |
| Total % weight/weight | 100.0 | 100.0 | 100.0 | 100.0 | 100.0 |

The invention claimed is:

1. A pharmaceutical composition for oral administration, the composition being a tablet not including microcrystalline cellulose 101 and having:
   an intragranular phase comprising:
   at least 250 mg of active agent 4-amino-5-fluoro-3-[6-(4-methylpiperazin-1-yl)-1H-benzimidazol-2-yl]-1H-quinolin-2-one monolactate monohydrate, in an amount of 40 to 65% by weight,
   a filler selected from the group consisting of MCC102, MCC105, MCC200, and combinations thereof, wherein the filler is in an amount of 30 to 60% by weight,
   one or more disintegrants in an amount of 1 to 15% by weight, and
   silicon dioxide and magnesium stearate in an amount of 0.1 to 10% by weight; and,
   an extragranular phase comprising 0.2 to 1% silicon dioxide, 1 to 3% magnesium stearate, and lacking microcrystalline cellulose,
   wherein:
   the composition exhibits bioequivalence at a 90% confidence interval to a capsule composition comprising 34% of a lactic acid salt of 4-amino-5-fluoro-3-[6-(4-methylpiperazin-1-yl)-1H-benzimidazol-2-yl]-1H-quinolin-2-one, 4% w/w crospovidone, 1% silicon dioxide, 60% microcrystalline cellulose, and 1% magnesium stearate;
   at least 90% of the active agent is released from the composition within 10 minutes as determined using USP apparatus 2 (Rotary Paddle) at a stirring rate of 50 rpm at 37° C. in 0.04 M HCl, 2 g/L NaCl, pH 1.5; and,
   at least 80% of the active agent is released from the composition within 10 minutes as determined using USP apparatus 2 (Rotary Paddle) at a stirring rate of 50 rpm at 37° C. in pH 4.5 acetate buffer.

2. The pharmaceutical composition of claim 1 wherein the disintegrant is not croscarmellose sodium.

3. The pharmaceutical composition according to claim 1 wherein the disintegrant is Crospovidone XL.

4. The pharmaceutical composition according to claim 1 wherein the disintegrant is present in an amount above 5% to 8% by weight.

5. The pharmaceutical composition according to claim 1 wherein the silicon dioxide is present in the intragranular phase in the amount of 0.5 to 2% by weight and the magnesium stearate is present in the intragranular phase in the amount of 1 to 4% by weight.

6. A process for the production of a composition as claimed in claim 1 which process is carried out under substantially dry conditions using granulation.

7. A process for the production of a composition as claimed in any one of the preceding claim which process comprises:
   i) preparing a mixture of 4-amino-5-fluoro-3-[6-(4-methylpiperazin-1-yl)-1H-benzimidazol-2-yl]-1H-quinolin-2-one monolactate monohydrate, one or more filler, disintegrant and glidant;
   ii) sieving the mixture;
   iii) adding lubricant;
   iv) processing the mixture of step (iii) by roller compaction;
   v) blending milled granulate of step (iv) with glidant, filler and disintegrant and mixing
   vi) lubricating with a lubricant; and,
   vii) forming tablets by compression.

8. The composition of claim 1 or process of claim 7, wherein the lactic acid salt of 4-amino-5-fluoro-3-[6-(4-methylpiperazin-1-yl)-IH-benzimidazol-2-yl]-IH-quinolin-2-one is Form $H_4$.

* * * * *